United States Patent
Ando et al.

(10) Patent No.: US 10,456,779 B2
(45) Date of Patent: Oct. 29, 2019

(54) PIPETTE TIP HAVING A STRAIGHT PIPE SECTION WITH INNER PROTRUSION AND PIPETTING METHOD FOR A LIQUID INCLUDING CELLS

(71) Applicant: Panasonic Corporation, Osaka (JP)

(72) Inventors: Takeshi Ando, Kyoto (JP); Toshinori Hirose, Osaka (JP); Toshiaki Yamauchi, Kyoto (JP); Norihiro Shibata, Osaka (JP)

(73) Assignee: Panasonic Corporation, Osaka (JP)

( * ) Notice: Subject to any disclaimer, the term of this patent is extended or adjusted under 35 U.S.C. 154(b) by 155 days.

(21) Appl. No.: 15/326,390

(22) PCT Filed: Dec. 17, 2015

(86) PCT No.: PCT/JP2015/006291
§ 371 (c)(1),
(2) Date: Jan. 13, 2017

(87) PCT Pub. No.: WO2016/147239
PCT Pub. Date: Sep. 22, 2016

(65) Prior Publication Data
US 2017/0203290 A1 Jul. 20, 2017

(30) Foreign Application Priority Data
Mar. 16, 2015 (JP) .................. 2015-051946

(51) Int. Cl.
*B01L 3/02* (2006.01)
*G01N 1/14* (2006.01)
(Continued)

(52) U.S. Cl.
CPC ............ *B01L 3/0275* (2013.01); *G01N 1/14* (2013.01); *B01L 2200/0647* (2013.01); *G01N 2035/0434* (2013.01); *G01N 2035/103* (2013.01)

(58) Field of Classification Search
None
See application file for complete search history.

(56) References Cited

U.S. PATENT DOCUMENTS 4,917,274 A    4/1990 Asa et al.
5,171,537 A * 12/1992 Wainwright .......... B01L 3/0275
                                                     422/514
(Continued)

FOREIGN PATENT DOCUMENTS

JP       7-284674      10/1995
JP    2005-091105       4/2005
(Continued)

OTHER PUBLICATIONS

The Extended European Search Report dated Dec. 20, 2017 for the related European Patent Application No. 15885337.4.
(Continued)

*Primary Examiner* — Christopher Adam Hixson
*Assistant Examiner* — Michelle Adams
(74) *Attorney, Agent, or Firm* — Panasonic IP Management; Kerry S. Culpepper (57) ABSTRACT

A pipette tip includes a main body section; and a straight pipe section disposed at the leading end of the main body section, in which the inner diameter of the straight pipe section is 0.8 mm to 1.5 mm inclusive, and the length of the straight pipe section is 5 mm to 15 mm inclusive.

11 Claims, 9 Drawing Sheets

(51) Int. Cl.
*G01N 35/04* (2006.01)
*G01N 35/10* (2006.01)

(56) References Cited

U.S. PATENT DOCUMENTS

| | | | |
|---|---|---|---|
| 5,876,918 A * | 3/1999 | Wainwright | B01L 3/0275 |
| | | | 210/198.2 |
| 6,565,728 B1 * | 5/2003 | Kozulic | B26D 7/1818 |
| | | | 204/606 |
| 2006/0048367 A1 | 3/2006 | Ishihama et al. | |
| 2007/0015276 A1 | 1/2007 | LeBlanc et al. | |
| 2010/0163111 A1 * | 7/2010 | Tajima | B01L 3/021 |
| | | | 137/3 |
| 2012/0009100 A1 | 1/2012 | Kirste et al. | |
| 2012/0071643 A1 * | 3/2012 | Helfer | B01L 3/0275 |
| | | | 536/25.4 |
| 2013/0280423 A1 | 10/2013 | Kirste et al. | |
| 2015/0182877 A1 * | 7/2015 | Yabuhara | G01N 30/08 |
| | | | 73/863.23 |
| 2015/0323426 A1 * | 11/2015 | Ito | C12M 33/04 |
| | | | 435/30 |
| 2015/0353884 A1 | 12/2015 | Ozaki et al. | |

FOREIGN PATENT DOCUMENTS

| | | | | |
|---|---|---|---|---|
| JP | 2012-073227 | 4/2012 | | |
| JP | 2014-018185 | 2/2014 | | |
| WO | WO-2014091525 A1 * | 6/2014 | | C12M 33/04 |
| WO | 2014/115799 | 7/2014 | | |

OTHER PUBLICATIONS

International Search Report of PCT application No. PCT/JP2015/006291 dated Mar. 15, 2016.
Center for iPS Cell Research and Application, Institute for Integrated Cell-Material Sciences, Kyoto University, "Method for Establishing Human iPS Cell", CiRA|M&M, [online], Jul. 4, 2008, Ver.1, [retrieved on Mar. 3, 2016], <URL:https://www.cira.kyoto-u.ac.jp/j/research/img/protocol/hiPS_Protocol_080703a.pdf>, pp. 5, 6 and 13.
Communication pursuant to Article 94(3) EPC dated Aug. 3, 2018 for the related European Patent Application No. 15885337.4.

* cited by examiner

| | | LENGTH mm | | | | |
|---|---|---|---|---|---|---|
| | | 0 | 5 | 10 | 15 | 20 |
| INNER DIAMETER mm | 0.5 | × | × | × | × | × |
| | 0.7 | × | × | × | × | × |
| | 0.8 | × | ○ | ○ | ○ | × |
| | 1.0 | × | ◎ | ◎ | ◎ | ○ |
| | 1.5 | × | ◎ | ◎ | ◎ | ○ |
| | 1.6 | × | × | × | × | × |

PIPETTE TIP HAVING A STRAIGHT PIPE SECTION WITH INNER PROTRUSION AND PIPETTING METHOD FOR A LIQUID INCLUDING CELLS

CROSS-REFERENCE TO RELATED APPLICATIONS

This application is a U.S. national stage application of the PCT International Application No. PCT/JP2015/006291 filed on Dec. 17, 2015, which claims the benefit of foreign priority of Japanese patent application No. 2015-051946 filed on Mar. 16, 2015, the contents all of which are incorporated herein by reference.

TECHNICAL FIELD

The present invention relates to a pipette tip used at the time of culturing cells, and a pipetting method using the pipette tip.

BACKGROUND ART

For culturing cells, a pipette and a pipette tip fitted in the leading end portion of the pipette are frequently used in order to suck, transport, and discharge a chemical solution. Accordingly, a pipette tip has been developed, which aims to prevent a liquid drip at the time of transporting the chemical solution and prevent the liquid exhaustion at the time of discharging the chemical solution. Specifically, a pipette tip is suggested, which prevents a liquid drip at the time of transporting the solution by configuring the leading end of a tip to have a double structure (for example, refer to PTL 1).

Also, a pipette tip is suggested, which enhances water repellency and improves liquid exhaustion by causing the leading end of the pipette tip to have two types of the surface roughness (for example, refer to PTL 2).

CITATION LIST

Patent Literature

PTL 1 Japanese Patent Unexamined Publication No. 2005-91105
PTL 2 Japanese Patent Unexamined Publication No. 2012-73227

SUMMARY OF THE INVENTION

Technical Problem

However, in the conventional pipette tip, liquid exhaustion and liquid drip of the chemical solution in the pipette has been only highlighted, and there is a problem in that a tip shape, in other words, an irregularity of a diameter has not been sufficiently reviewed, from a viewpoint of cell breakage (reducing the size of cell aggregation (colony), or making the cell aggregation into a single cell) by means of pipetting, which is an action of repeating sucking and discharging the chemical solution, and is another role of the pipette.

An object of the present invention is to realize a pipette tip and a pipetting method, which can break cells within a cell suspension into an aggregation of the target size or a single cell with less irregularity of the diameter.

Solutions to Problem

In order to achieve the object, a pipette tip according to an aspect of the present invention includes a main body section; and a straight pipe section disposed at a leading end of the main body section, in which an inner diameter of the straight pipe section is 0.8 mm to 1.5 mm inclusive, and a length of the straight pipe section is 5 mm to 15 mm inclusive.

In addition, in order to achieve the object, a pipetting method according to another aspect of the present invention includes sucking a liquid including cells using the pipette tip; and discharging the sucked liquid using the pipette tip.

Advantageous Effect of Invention

As described above, by using the pipette tip according to the aspect of the present invention, it is possible to break cells within a cell suspension into an aggregation with a target size or a single cell such that the irregularity of the diameter is smaller.

DESCRIPTION OF EMBODIMENTS

Hereinafter, an embodiment of the present invention will be described using drawings. In addition, the same reference numeral will be attached to the same constituent element and the description thereof may be omitted. Each constituent element is used mainly for schematically illustrating the drawings in order for an easy understanding.

Embodiment 1

Figure 1A:
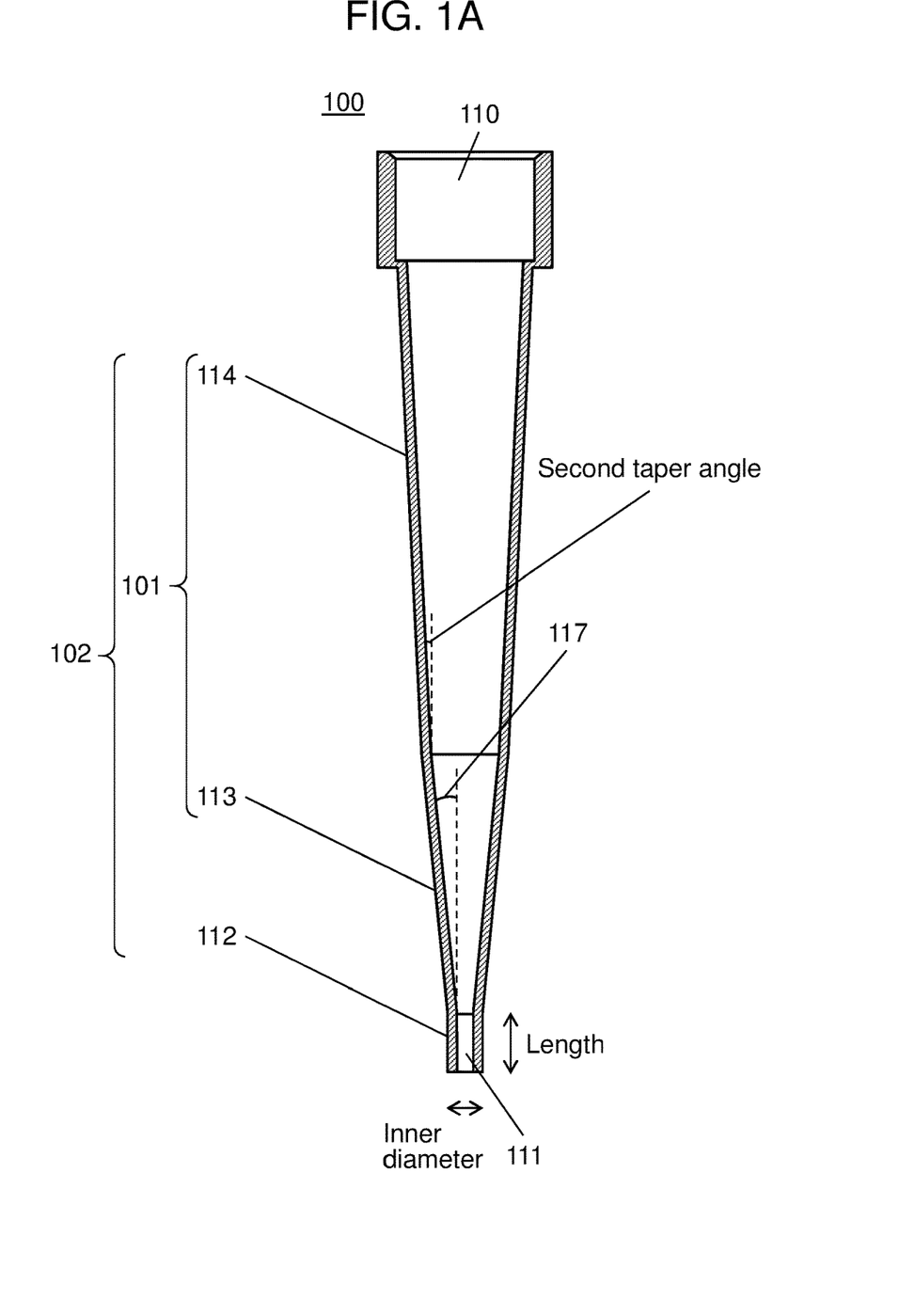
FIG. 1A is a cross-sectional view of a pipette tip.
Figure 1B:
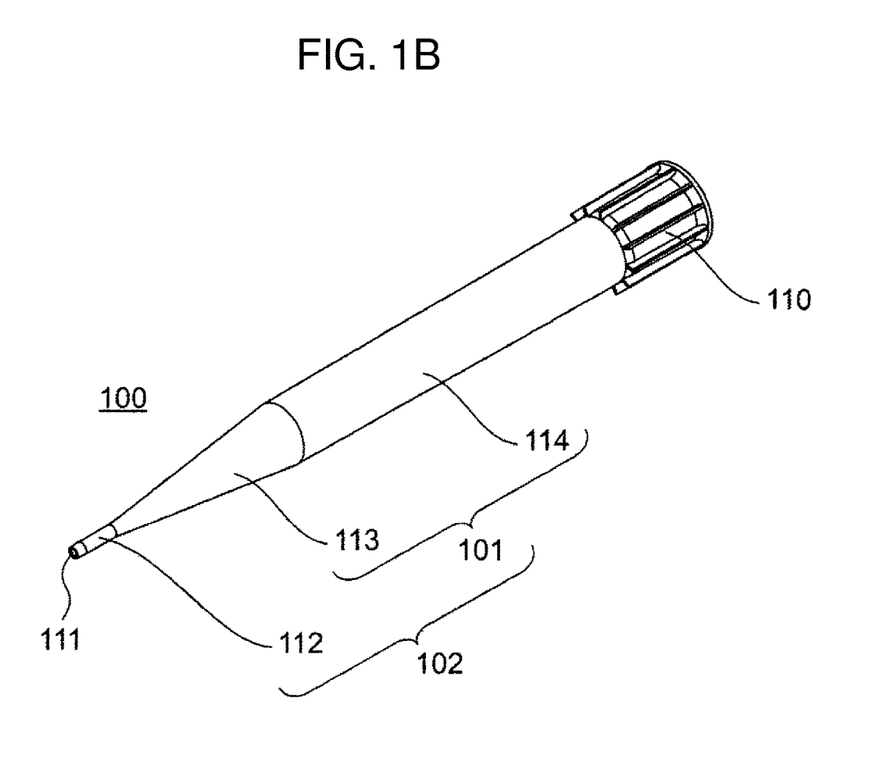
FIG. 1B is a perspective view of a pipette tip.

FIG. 1A is a cross-sectional view schematically illustrating pipette tip 100 according to embodiment 1 of the present invention. FIG. 1B is a perspective view of the pipette tip.

Pipette tip 100 of the embodiment 1 is formed as a small tube as illustrated in FIG. 1A and FIG. 1B. At one end of the small tube, a relatively large opening (large opening 110) is included and at another end of the small tube (leading end), a relatively small opening (small opening 111) for passing through a liquid is included. Pass-through section 102 is included between large opening 110 and small opening 111.

Pass-through section 102 which is toward from small opening 111 to large opening 110 is configured to include main body section 101 of pipette tip 100 and straight pipe section 112 disposed at the leading end of main body section 101. Main body section 101 is configured to include first taper section 113 and second taper section 114. Accordingly, pipette tip 100 is configured such that straight pipe section 112, first taper section 113, and second taper section 114 are adjacent to each other so as to be integrally connected from another end to one end. Straight pipe section 112 is not inclined and is a tube portion whose inner diameter is constant. The inclination angle of first taper section 113 is greater than the inclination angle of second taper section 114.

Figure 2:
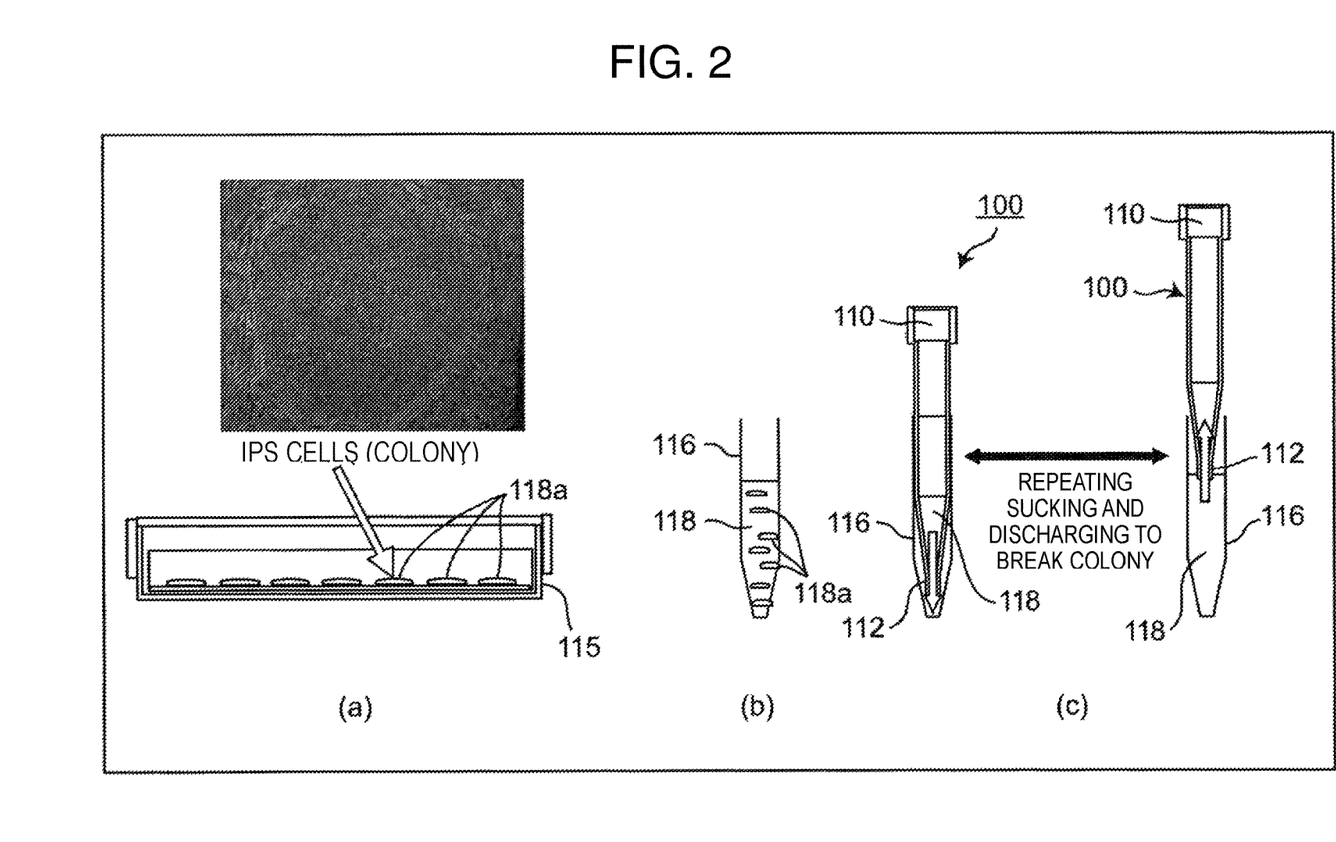
FIG. 2 is a view illustrating a state of colony breakage by pipetting.

One role of pipette tip 100 is cell breakage by means of pipetting. The cell breakage by means of pipetting will be described based on the sections (a), (b), and (c) of FIG. 2. The section (a) of FIG. 2 is a view describing a state where cells 118a are attached to the inside of culture vessel 115. The section (b) of FIG. 2 is a view describing a state where cells 118a are peeled off and collected from culture vessel 115 to be cell suspension 118 in centrifuge tube 116. The section (c) of FIG. 2 is a view describing a state where a colony within cell suspension 118 is being broken by means of pipetting. Cell suspension 118, in which solid 118a such as cells and a liquid such as a culture fluid and a release agent, which is a chemical solution for peeling off the cells attached to culture vessel 115 are mixed to each other, is collected from culture vessel 115 shown in the section (a) of FIG. 2 using pipette tip 100 to put into centrifuge tube 116 (refer to the section (b) of FIG. 2). Next, by sucking and discharging cell suspension 118 between centrifuge tube 116 and pipette tip 100 one time or more, while moving pipette tip 100 in an axial direction in centrifuge tube 116 in a state where pipette tip 100 is inserted in this centrifuge tube 116, the size of a cell aggregation (colony) in cell suspension 118 is made to be small or the cell aggregation is made into a single cell. This operation is referred to as cell breakage by means of pipetting.

This cell breakage by means of pipetting is conduced when an operation is necessary, which classifies a cell strain as cells 118a within culture vessel 115 are almost in a saturated state (hereinafter, referred to as subculture), or a measurement of the number of cells is necessary in order to accurately control the cell density at the time of seeding the cells. At this time, as one example, by executing an pipetting operation while moving pipette tip 100 in centrifuge tube 116 having a capacity of 15 ml, an outer diameter of about 18 mm, and a length of about 120 mm, the cells can be effectively broken. Also, the position of small opening 111 at the leading end of pipette tip 100 in centrifuge tube 116 preferably descends as the suspension is sucked and preferably ascends as the suspension is discharged so as to be the same level as the liquid surface of cell suspension 118. Accordingly, it is possible to suppress generation of unnecessary foam at the time of pipetting.

In the cell breakage by means of pipetting, the inner diameter (diameter on the inner side) and the length of straight pipe section 112 in FIG. 1A and FIG. 1B are important conditions, in order to break the cell aggregation into a desired size, by utilizing that a flow rate at the time of sucking and discharging a liquid including the cells becomes faster, in straight pipe section 112 rather than other sections.

It is necessary to classify human induced pluripotent stem (hereafter: "iPS") cells after the diameter of a colony (cell aggregation with a plurality of single cells aggregated) grown to have a diameter of about 1 mm is broken to have a diameter of 100 to 200 µm at the time of subculturing. The present inventors have used these human iPS cells and determined the optimal range of the inner diameter and the length of straight pipe section 112 by conducting a test of breaking the cells with trial and error. In the test, a DMEM F-12 is used as a culture medium and CTK is used as a release agent. When breaking the human iPS cells, in a case where the diameter is smaller than 100 µm, the cell is likely to be extinct and in a case where the diameter is larger than 200 µm, an undifferentiated state, which is a characteristic of the iPS cells, is likely to be lost. Therefore, in a case where the number of colonies whose diameter is in the range of 100 µm to 200 µm inclusive is 70% or more with respect to the total number of colonies in the cell suspension after pipetting, this case is regarded as a success in the cell breakage by means of pipetting, and other cases are regarded as a failure, and the test is executed. The condition of the pipetting method in this test is that sucking and discharging are performed in the amount of 9 ml with respect to 10 ml of the cell suspension, at the sucking and discharging rate of 4 ml/s three times. The projected area of the colony is converted into a particle of a circle using a geometrical formula so as to obtain the diameter of the colony as a particle diameter (equivalent diameter) of the particle of the circle.

Figure 6:
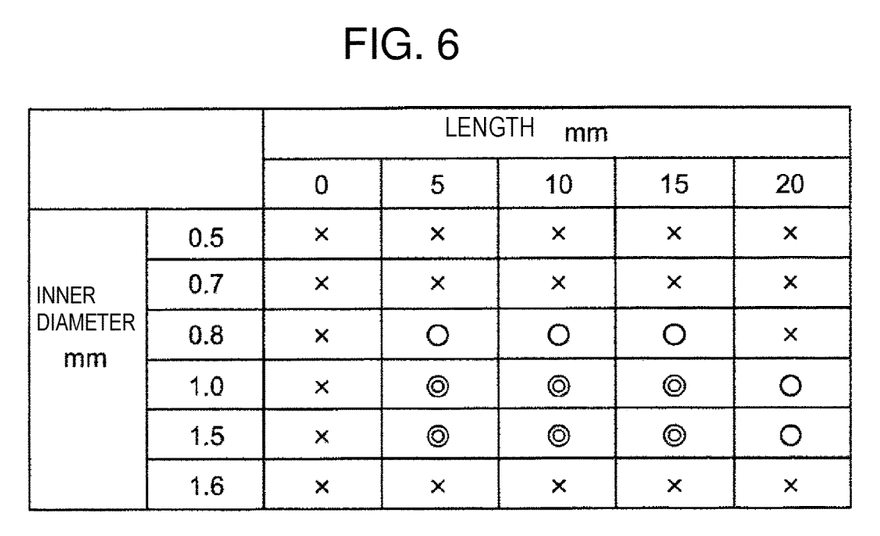
FIG. 6 is a view illustrating a result of the colony diameter when the inner diameter and the length of the straight pipe section are changed to conduct pipetting.

FIG. 6 illustrates a result of the colony diameter when the values of the inner diameter and the length of straight pipe section 112 (FIG. 1A and FIG. 1B) are changed with trial and error to perform pipetting. In FIG. 6, x represents a failure, single circle of "○" represents a success (a colony having a diameter of 100 to 200 µm inclusive is 70% or more of the total colonies), and double circle represents a success (a colony having a diameter of 100 to 200 µm inclusive is 80% or more of the total colonies).

From the result of FIG. 6, it is understood that each of the following conditions are successful in which when the inner diameter of straight pipe section 112 in FIG. 1A and FIG. 1B is 0.8 mm, the length thereof is 5 mm to 15 mm inclusive, when the inner diameter is 1.0 mm, the length thereof is 5 mm to 20 mm inclusive, and when the inner diameter is 1.5 mm, the length thereof is 5 mm to 20 mm inclusive. However, since it is understood that it is difficult to form straight pipe section 112 to have the length of 20 mm without bending and with the thickness to be thin and a liquid cannot be sucked sufficiently, which is an important function of the pipette, a condition of the length of 20 mm is excluded. Therefore, the upper limit of the length of straight pipe section 112 is set to 15 mm in consideration of allowance in the length.

As described above, it is understood that the optimal condition of straight pipe section 112 is that the inner diameter is 0.8 mm to 1.5 mm inclusive and the length is 5 mm to 15 mm inclusive. By including straight pipe section 112 having the inner diameter and the length within this optima range, it is possible to break the irregularity of the colony diameter to be smaller by performing pipetting in a small number of times.

Furthermore, according to the result of FIG. 6, the inner diameter of straight pipe section 112 of FIG. 1A and FIG. 1B may be set to 1.0 mm to 1.5 mm inclusive. In a case of the above condition, the colony diameter after pipetting is in the range of 100 to 200 µm inclusive, which is further stabilized.

Figure 3:
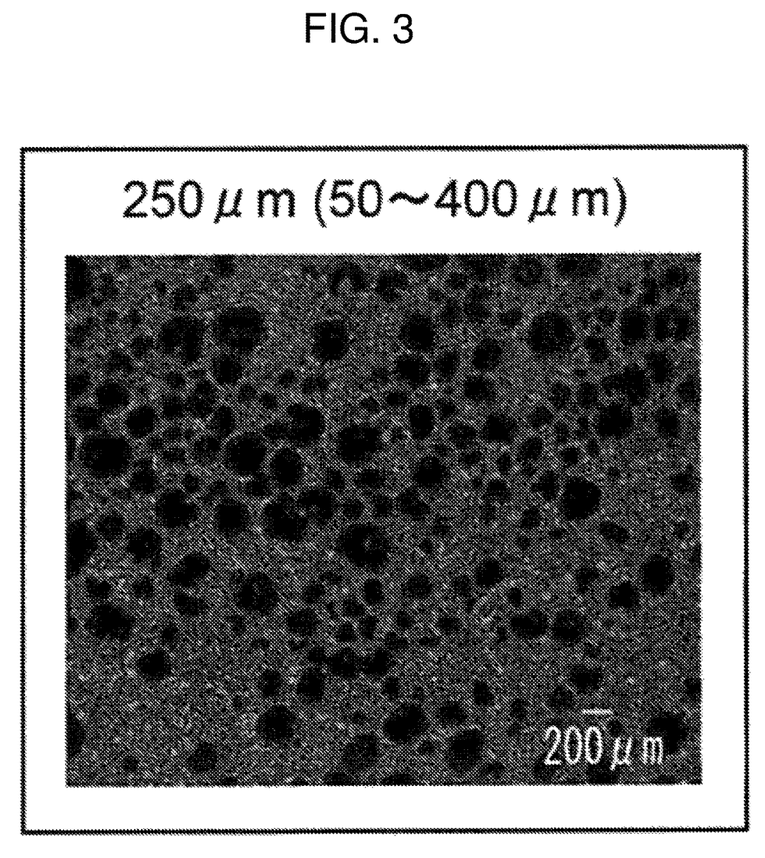
FIG. 3 is a view illustrating a colony photomicrograph (a length of 0 mm and an inner diameter of 0.8 mm of straight pipe section 112) after pipetting (250 μm in this view indicates an arithmetic mean value and 50 to 400 μm indicates a minimum value to a maximum value).

In addition, in a case where the length of straight pipe section 112 is shorter than 5 mm, the colony itself is broken but the irregularity of the colony diameter becomes greater. For example, FIG. 3 illustrates a photomicrograph of pipetting when the length of straight pipe section 112 is set to 0 mm (inner diameter of 0.8 mm). When the colony of FIG. 3 is measured, it is understood that the irregularity becomes greater, in which the arithmetic mean is 250 µm and 50 to 400 µm with respect to the target of 100 to 200 µm. At this time, the ratio of the colony whose diameter is in the range of 100 µm to 200 µm inclusive is 50% with respect to the total colonies.

Figure 4:
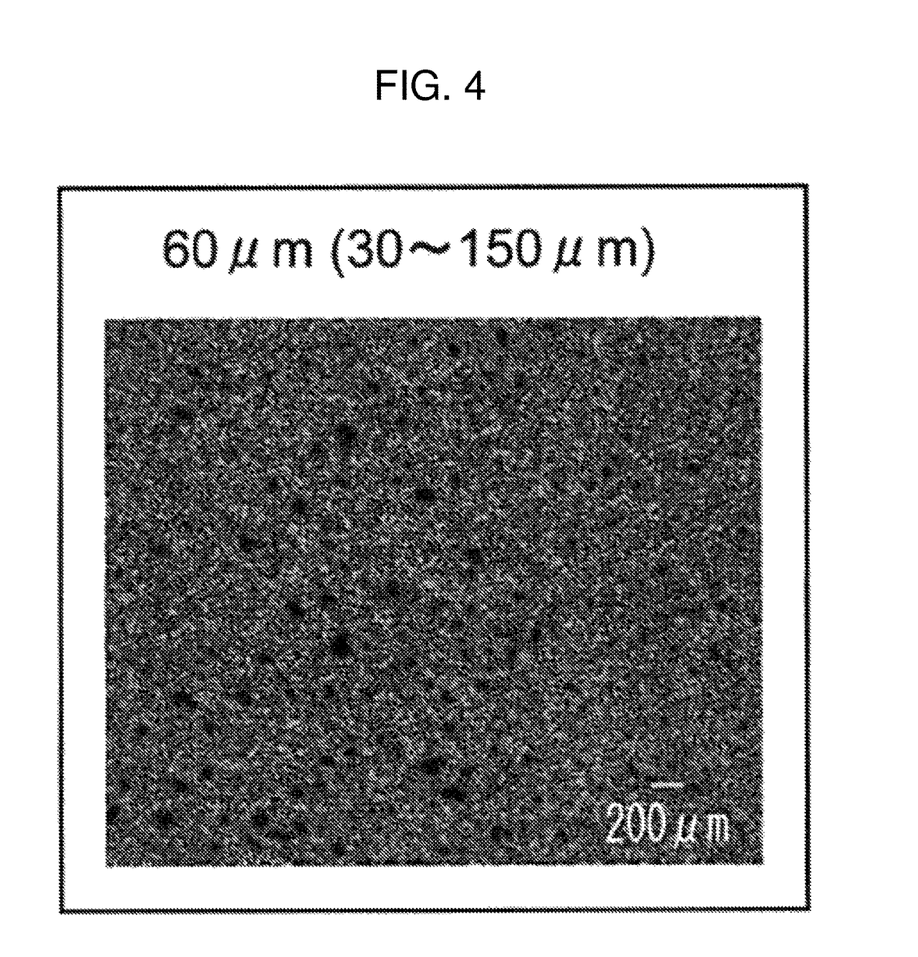
FIG. 4 is a view illustrating a colony photomicrograph (a length of 5 mm and an inner diameter of 0.7 mm of straight pipe section 112) after pipetting (60 μm in this view indicates an arithmetic mean value and 30 to 150 μm indicates a minimum value to a maximum value).
Figure 5:
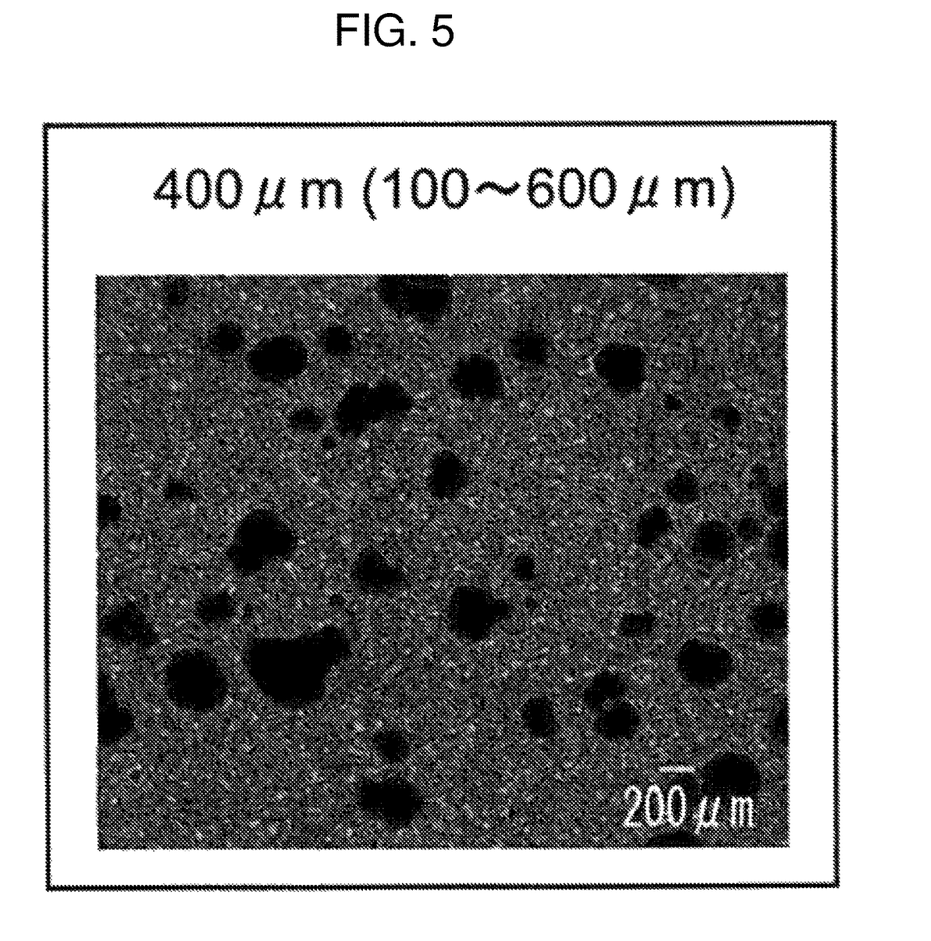
FIG. 5 is a view illustrating a colony photomicrograph (a length of 5 mm and an inner diameter of 1.6 mm of straight pipe section 112) after pipetting (400 μm in this view indicates an arithmetic mean value and 100 to 600 μm indicates a minimum value to a maximum value).

In a case where the inner diameter of straight pipe section 112 of FIG. 1A and FIG. 1B is less than 0.8 mm, the colony is broken too much and on the other hand, in a case where the inner diameter is greater than 1.5 mm, there is a problem in that the colony is not broken. FIG. 4 and FIG. 5 respectively illustrate a photomicrograph after pipetting when the inner diameter of straight pipe section 112 is 0.7 mm (a length of 5 mm) and a photomicrograph after pipetting when the inner diameter of straight pipe section 112 is 1.6 mm (a length of 5 mm). An arithmetic mean of the colony diameter in FIG. 4 is 60 µm, a distribution is 30 to 150 µm, and the ratio of the colony whose diameter is 100 µm to 200 µm inclusive is 30% with respect to the total colonies. In addition, an arithmetic mean of the colony diameter in FIG. 5 is 400 µm, a distribution is 100 to 600 µm, and the ratio of the colony whose diameter is in the range of 100 µm to 200 µm inclusive is 30% with respect to the total colonies.

Figure 7:
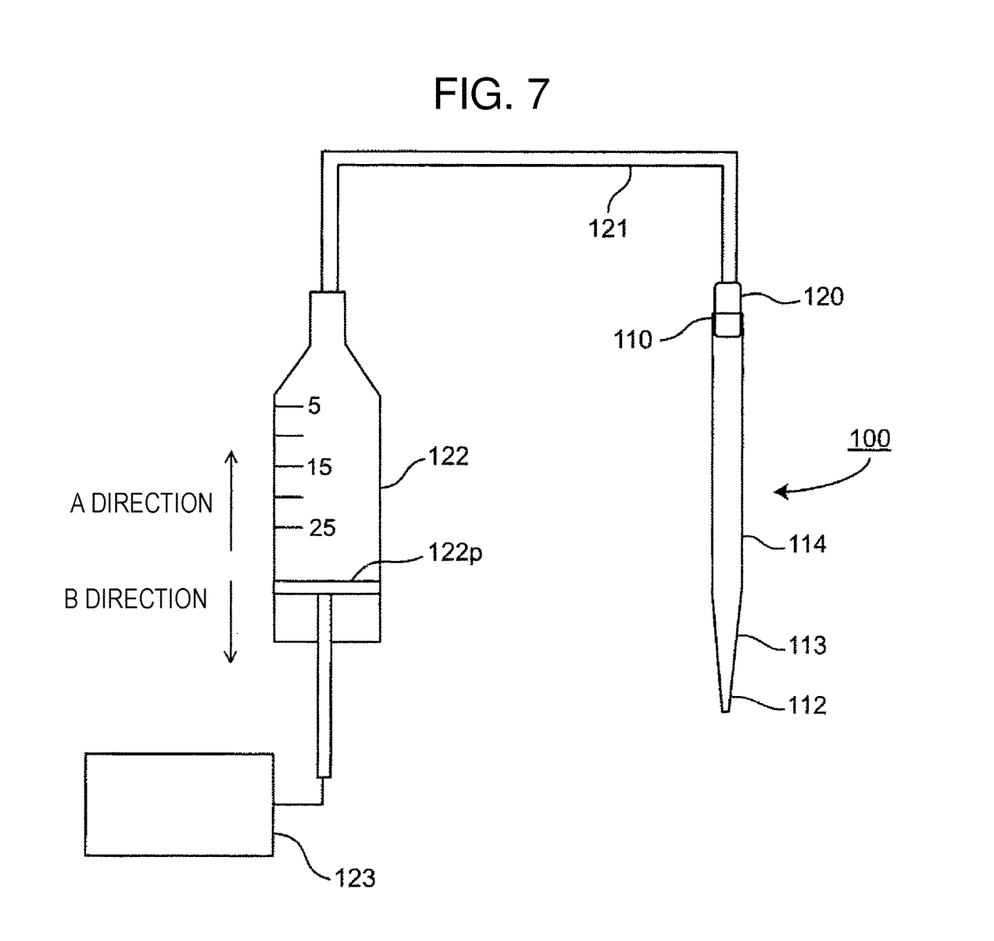
FIG. 7 is a view describing a sucking and discharging method using the pipette tip.

Here, FIG. 7 illustrates a configuration view of a system for sucking and discharging a liquid using pipette tip 100. The system is configured to include coupling section 120 with large opening 110 fitted in, tube 121 connected to coupling section 120, syringe pump 122 connected to tube 121, and control section 123. Control section 123 is driven to control the position of piston 122p of syringe pump 122 to move in a reciprocating manner, thereby performing sucking and discharging a liquid in pipette tip 100 caused by the driving of syringe pump 122. Control section 123 controls piston 122p within syringe pump 122 to move in an A direction of FIG. 7 such that the atmospheric pressure within syringe pump 122 is decreased at the time of sucking. Control section 123 controls piston 122p within syringe pump 122 to move in a B direction of FIG. 7 such that the atmospheric pressure within syringe pump 122 is increased at the time of discharging.

The material of pipette tip 100 is a resin material such as polypropylene or polystyrene. The resin material may be a material which can endure a disinfection treatment using electron beams, a disinfection treatment using gamma rays for a sterilization treatment, or an autoclave treatment.

Straight pipe section 112 is described as a circular tube portion having a constant size of the inner diameter and a constant size of the outer diameter, but the straight pipe section 112 is not limited to this and may be configured as follows.

Figure 8:
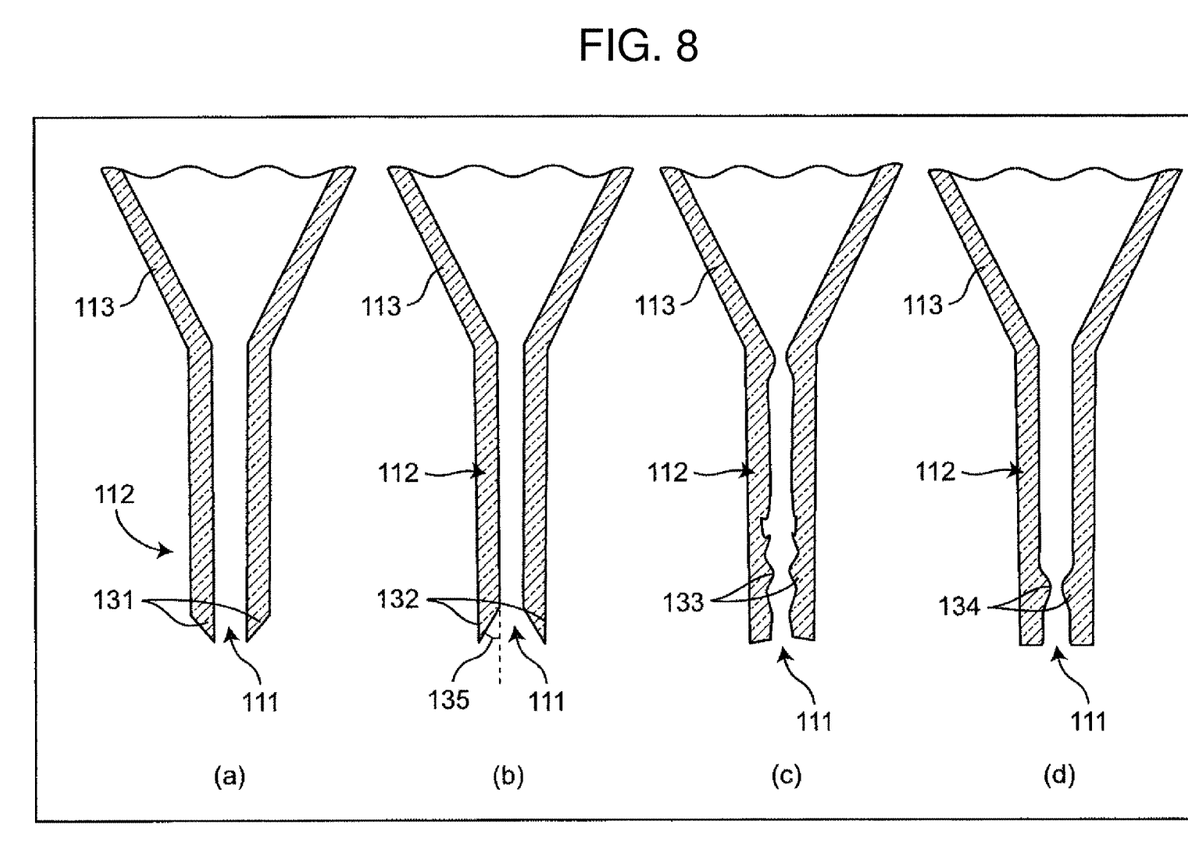
FIG. 8 is a cross-sectional view of the leading end of the pipette tip.

For example, as illustrated in the section (a) of FIG. 8, the thickness between the inner wall and the outer wall of small opening 111 of straight pipe section 112 may be forefront 131, which becomes thinner as small opening 111 approaches the leading end thereof, and the inner diameter may be the same as it is. That is, the outer diameter of straight pipe section 112 may be configured to be reduced toward the leading end. Due to this, liquid exhaustion at the time of sucking and discharging a liquid is improved.

Also, as illustrated in the section (b) of FIG. 8, the thickness between the inner wall and the outer wall of small opening 111 of straight pipe section 112 may be reverse taper section 132 having taper angle 135, which becomes thinner as small opening 111 approaches the leading end thereof, and the outer diameter may be the same as it is. That is, straight pipe section 112 may have reverse taper section 132 whose inner diameter is expanded toward the leading end. Taper angle 135 is desirably 3 degrees to 60 degrees inclusive. Due to this, cells can be effectively collected at the time of sucking a cell suspension and a colony can be broken taking a small number of times. In a case where taper angle 135 is smaller than 3 degrees, it is difficult to collect cells, and in a case where the taper angle is greater than 60 degrees, the cells are likely to be caught by reverse taper section 132 and the cells cannot be collected sufficiently.

Also, as illustrated in the section (c) of FIG. 8, unevenness 133 may be disposed on the inner wall of straight pipe section 112. Unevenness 133 is an extremely small unevenness having a peak of about 0.2 mm and a pitch of about 0.2 mm, and makes the surface roughness of the inner wall bigger. Due to this, it is possible to effectively break a colony to have a diameter of 100 to 200 µm inclusive, which is an optimal colony diameter when culturing a colony of human iPS cells.

Also, as illustrated in the section (d) of FIG. 8, protrusion 134 may be provided to the inner wall of straight pipe section 112 so as to make the inner diameter of the part where the inner diameter is the narrowest because of protrusion 134 to be 200 µm. It is possible to effectively break the cells to have a diameter of 100 to 200 µm, which is an optimal colony diameter when culturing a colony of human iPS cells owing to protrusion 134.

Here, taper angle 117 of first taper section 113 connected to straight pipe section 112 illustrated in FIG. 1A and FIG. 1B is desirably 3 degrees to 20 degrees inclusive. If the taper angle is smaller than 3 degrees, a vortex is unlikely to occur in first taper section 113 at the time of sucking a cell suspension, and a cell colony is unlikely to be mixed in a homogeneous manner. On the other hand, if the taper angle is greater than 20 degrees, cells are likely to be stayed at the joint of first taper section 113 and second taper section 114, and the cell breakage cannot be realized sufficiently. By adopting first taper section 113 with taper angle 117 of the aforementioned range, a colony can be mixed in a homogenous manner at the time of pipetting and an irregularity of the colony diameter can be reduced, in other words, cells can be broken into a uniform diameter.

The length of first taper section 113 is desirably 20 mm to 100 mm inclusive. In a case where the length is shorter than 20 mm, since a vortex generated in first taper section 113 is too strong, cells are greatly damaged. On the other hand, in a case where the length is longer than 100 mm, a vortex is unlikely to be generated in first taper section 113, and it is difficult to mix the cells in a homogeneous manner. By using pipette tip 100 having first taper section 113 whose length is in the aforementioned range, when adjusting a colony diameter to a desired diameter by means of pipetting, it is possible to reduce damage to cells and mix the cells in a homogeneous manner while reducing the irregularity of the colony diameter.

The outer diameter and the inner diameter of the connection section (boundary) between first taper section 113 and second taper section 114 is desirably 10 mm to 20 mm inclusive. Straight pipe section 112 has a role of breaking a cell aggregation (colony), first taper section 113 has a role of breaking the cell aggregation and homogenizing, and second taper section 114 has a role of increasing the sucking and discharging amount at the time of pipetting. Thus, in a case where the inner diameter of the connection section between first taper section 113 and second taper section 114 is smaller than the aforementioned range, the total length of pipette tip 100 becomes too long and a pipetting operation becomes difficult. On the other hand, in a case where the outer diameter of the connection section is greater than the aforementioned range, second taper section 114 is likely to be in contact with the inner wall of centrifuge tube 116 (FIG. 2) having a capacity of 15 ml and pipetting becomes difficult. In addition, in order for second taper section 114 to have a function of increasing the sucking and discharging amount at the time of pipetting, taper angle is desirably small without any limitations. From the above, use of pipette tip 100 in which the diameter of the connection section between first taper section 113 and second taper section 114 is within the aforementioned range enables to execute pipetting easily.

The inner diameter of second taper section 114 may be greater as much as possible within the range of 10 mm to 18 mm inclusive. Increase of the capacity of pipette tip 100 in second taper section 114 enables to shorten the total length of pipette. Due to this, an operator or a robot handling pipette tip 100 is able to conduct a pipette operation easily.

The total length of pipette tip 100 is, for example, 60 mm to 170 mm inclusive. Due to this, when an operation such as pipetting is conducted within centrifuge tube 116 (FIG. 2) having a capacity of 15 ml, it is possible to reduce a burden to an operator or a robot conducting the operation from a viewpoint of a movable area. In other words, in a case of an operator, the pipette can be easily inserted into centrifuge tube 116 and in a case of a work robot, the overall height of the entire devices can be decreased.

In a case where a colony of the human iPS cells is broken by pipetting, it is desirable to repeat sucking and discharging 5 ml to 12 ml inclusive of a cell suspension 2 times to 5 times inclusive at a rate of 3.0 ml/s to 7.0 ml/s inclusive (both of sucking and discharging) using pipette tip 100. The amount and the rate of sucking and the amount and the rate of discharging of pipette tip 100 are controlled by control section 123 of FIG. 7. The aforementioned pipetting condition is found out from the test of the inventors. Specifically, it is understood that if the rate of sucking and discharging is smaller than the aforementioned range, the cell aggregation could not be broken gently. Also, if the rate of sucking and discharging is greater than the aforementioned range, the broken cells are greatly damaged. If the amount of sucking and discharging is smaller than the aforementioned range, the cell aggregation is not mixed in a homogenous manner and if the amount of sucking and discharging is greater than the aforementioned range, the liquid overflows from large opening 110 of pipette tip 100 and may be contaminated. If the number of performing sucking and discharging is smaller than the aforementioned range, the irregularity of the colony diameter becomes greater and if the number of performing sucking and discharging is greater than the aforementioned range, the cells are greatly damaged. From the above, by executing pipetting under the aforementioned conditions, a shearing force generated from sucking and discharging the cell suspension can reduce damage to the cells and realize the cell breakage in a homogeneous manner, while reducing the irregularity of the colony diameter.

According to the embodiment, at least, pipette tip 100 is configured such that the inner diameter of straight pipe section 112 is 0.8 mm to 1.5 mm inclusive and the length of straight pipe section 112 is 5 mm to 15 mm inclusive. Due to this configuration, cells 118a in cell suspension 118 can be broken into an aggregation of the target size or a single cell with less irregularity of the colony diameter.

Also, the aforementioned effect can be exhibited by realizing a pipetting method, in which a liquid including cells is sucked using pipette tip 100 and the sucked liquid is discharged using pipette tip 100.

When the pipetting method is executed, the aforementioned effect can be exhibited more remarkably by sucking and discharging 5 ml to 12 ml inclusive of the liquid only 2 times to 5 times inclusive at a rate of 3.0 ml/s to 7.0 ml/s inclusive.

Furthermore, by applying the human iPS cells to the cells and executing the pipetting method with respect to a liquid including the human iPS cells, it is possible to break the diameter of the colony formed by the human iPS cells into 100 μm to 200 μm inclusive. That is, the human iPs cells in cell suspension 118 can be broken into an aggregation of the target size or a single cell with less irregularity of the colony diameter.

An appropriate combination of any embodiment or modification example among the aforementioned various embodiments or modification examples enables each effect thereof to be exhibited. Also, a combination between the embodiments, a combination between the examples, or a combination of the embodiment and example can be made, and a combination between the features of a different embodiment or example can be made.

INDUSTRIAL APPLICABILITY

According to the pipette tip and the pipetting method using the pipette tip of the present invention, cells in the cell suspension can be broken into an aggregation of the target size or a single cell with less irregularity of the diameter, and the pipette tip and the pipetting method using the pipette tip are useful in the field of a regenerative medicine used at the time of culturing cells or drug development.

The invention claimed is:

1. A pipette tip comprising:
   a main body section; and
   a straight pipe section connected to the main body section and disposed at a leading end of the pipette tip,
   wherein the main body section includes a first taper section whose diameter is reduced toward the straight pipe section and a second taper section connected to the first taper section,
   wherein an inner diameter of the straight pipe section is greater than or equal to 0.8 mm and less than or equal to 1.5 mm,
   a length of the straight pipe section is 5 mm to 15 mm inclusive,
   a protrusion is disposed on an inner wall of the straight pipe section, and
   the protrusion makes a narrowest inner diameter of the straight pipe section to be 200 μm.

2. The pipette tip of claim 1, wherein a taper angle of the first taper section is 3 degrees to 20 degrees inclusive.

3. The pipette tip of claim 1, wherein
   the first taper section is connected to the straight pipe section, and
   a taper angle of the first taper section connected to the straight pipe section is 3 degrees to 20 degrees inclusive.

4. The pipette tip of claim 1, wherein a length of the first taper section is 20 mm to 100 mm inclusive.

5. The pipette tip of claim 1, wherein an inner diameter of the second taper section is a range of 10 mm to 18 mm inclusive.

6. The pipette tip of claim 1,
   wherein a total length of the pipette tip is 60 mm to 170 mm inclusive.

7. The pipette tip of claim 1, wherein the first taper section is connected to the straight pipe section, and an inner diameter at the first taper section where the first taper section is connected to the straight pipe section is equal to an inner diameter of the straight pipe section.

8. A pipetting method comprising:
  sucking a liquid including cells using the pipette tip of claim 1; and
  discharging the sucked liquid using the pipette tip.

9. The pipetting method of claim 8, wherein 5 ml to 12 ml inclusive of the liquid is sucked and discharged 2 times to 5 times inclusive at a rate of 3.0 ml/s to 7.0 ml/s inclusive.

10. The pipetting method of claim 8, wherein the cells are human induced pluripotent stem (iPS) cells.

11. The pipetting method of claim 10,
  wherein the liquid including the human iPS cells is sucked using the pipette tip, and
  the sucked liquid is discharged using the pipette tip so as to break a colony formed by the human iPS cells into a colony having a diameter of 100 μm to 200 μm inclusive.

* * * * *